United States Patent
Ashibe et al.

(10) Patent No.: US 12,129,239 B2
(45) Date of Patent: Oct. 29, 2024

(54) METHOD FOR PRODUCING METHYLENE DISULFONATE COMPOUND

(71) Applicant: SUMITOMO SEIKA CHEMICALS CO., LTD., Hyogo (JP)

(72) Inventors: Seiya Ashibe, Hyogo (JP); Seiji Bando, Hyogo (JP); Yusaku Masuhara, Hyogo (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 59 days.

(21) Appl. No.: 17/629,167

(22) PCT Filed: Jul. 22, 2020

(86) PCT No.: PCT/JP2020/028366
§ 371 (c)(1),
(2) Date: Jan. 21, 2022

(87) PCT Pub. No.: WO2021/015219
PCT Pub. Date: Jan. 28, 2021

(65) Prior Publication Data
US 2022/0251059 A1    Aug. 11, 2022

(30) Foreign Application Priority Data

Jul. 23, 2019 (JP) .................................. 2019-135408

(51) Int. Cl.
*C07D 327/00* (2006.01)

(52) U.S. Cl.
CPC .................................. *C07D 327/00* (2013.01)

(58) Field of Classification Search
CPC .................................................. C07D 327/00
See application file for complete search history.

(56) References Cited

U.S. PATENT DOCUMENTS

| | | | |
|---|---|---|---|
| 2009/0137820 A1 | 5/2009 | Hiyama et al. | |
| 2013/0137881 A1 | 5/2013 | Bando et al. | |
| 2023/0150967 A1* | 5/2023 | Ashibe | C07D 327/00 |
| | | | 549/11 |

FOREIGN PATENT DOCUMENTS

| | | |
|---|---|---|
| CN | 102344436 A | 2/2012 |
| CN | 108840852 A | 11/2018 |
| IN | 2018-21043808 A | 7/2019 |
| JP | S61-501089 A | 5/1986 |
| JP | 2005-336155 A | 12/2005 |
| WO | 85/03075 A1 | 7/1985 |
| WO | 2007/125736 A1 | 11/2007 |
| WO | 2012/026266 A1 | 3/2012 |

OTHER PUBLICATIONS

A machine generated English translation of CN 1088840852 A to Zhao et al. (Year: 2018).*
Robinson et al., Canadian Journal of Chemistry, vol. 44 (1966), pp. 1437-1444. (Year: 1966).*
A machine generated English translation of CN 108840852 A to Zhao et al. (Year: 2018).*
International Search Report for PCT/JP2020/028366 dated Sep. 29, 2020 (PCT/ISA/210).

* cited by examiner

*Primary Examiner* — Laura L Stockton
(74) *Attorney, Agent, or Firm* — Sughrue Mion, PLLC

(57) ABSTRACT

Provided is a novel production method capable of easily producing a methylene disulfonate compound. The method for producing a methylene disulfonate compound comprises reacting a specific sulfonic acid compound with a formaldehyde compound in the presence of sulfur trioxide.

5 Claims, No Drawings

METHOD FOR PRODUCING METHYLENE DISULFONATE COMPOUND

CROSS REFERENCE TO RELATED APPLICATIONS

This application is a National Stage of International Application No. PCT/JP2020/028366 filed Jul. 22, 2020, claiming priority based on Japanese Patent Application No. 2019-135408 filed Jul. 23, 2019.

Technical Field

The present disclosure relates to a method for producing a methylene disulfonate compound and the like. The contents of all of the documents described in the present specification are incorporated herein by reference.

Background Art

Methylene disulfonate compounds are known to be useful in pharmaceutical products such as animal leukemia drugs; stabilizers for secondary battery electrodes; and the like.

For example, Patent Literature (PTL) 1 discloses a method for producing a methylene disulfonate compound by reacting silver disulfonate, which is obtained by reacting disulfonyl chloride with silver carbonate, with diiodomethane.

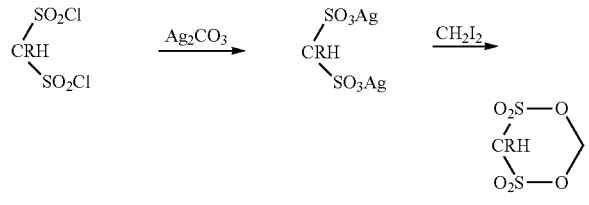

Further, for example, Patent Literature (PTL) 2 discloses a method for producing a methylene disulfonate compound by reacting an alkane disulfonic acid or the like with methylene diacetate or the like.

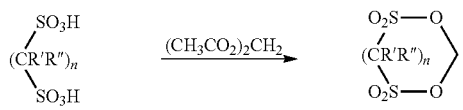

Further, for example, Patent Literature (PTL) 3 discloses a method for producing a methylene disulfonate compound by converting methanedisulfonic acid to methanedisulfonic acid chloride using a chlorinating agent such as thionyl chloride and then reacting the methanedisulfonic acid chloride with formaldehyde.

Citation List

Patent Literature

PTL 1: JPS61-501089A
PTL 2: JP2005-336155A
PTL 3: CN102344436A

Summary of Invention

Technical Problem

However, the method of Patent Literature (PTL) 1 has problems such that in addition to the method using expensive silver carbonate and diiodomethane, the reaction proceeds slowly, and the desired product may not be obtained with a satisfactory yield; furthermore, since a stoichiometric amount of poorly soluble silver iodide is produced as a byproduct, handleability in transfer and filtration processes may become a problem.

The method of Patent Literature (PTL) 2 has a problem such that the methylene diacetate to be used is difficult to obtain and expensive.

The method of Patent Literature (PTL) 3 has problems such that in addition to the method comprising a complicated production process, which is a multi-step reaction process, a chlorinating agent causes a side reaction that produces a toxic by-product.

As described above, none of the previously known methods can be considered to always be satisfactory production methods for industrial-scale mass production.

The present inventors conducted research in order to provide a novel production method capable of easily producing a methylene disulfonate compound. Specifically, the inventors found the possibility that a methylene disulfonate compound could be produced by reacting a sulfonic acid compound with a formaldehyde compound in the presence of sulfur trioxide ($SO_3$, also referred to as anhydrous sulfuric acid), and made further improvements.

The present disclosure encompasses, for example, the subjects described in the following items.

Item 1

A method for producing a methylene disulfonate compound, the method comprising reacting at least one sulfonic acid compound with a formaldehyde compound in the presence of sulfur trioxide, the sulfonic acid compound being selected from the group consisting of:

compounds represented by formula (1):

(wherein two Xs are the same or different and represent a hydrogen atom or an alkali metal;
$R^1$ and $R^2$ are the same or different and represent a $C_{1-4}$ alkyl group optionally substituted with one or more halogen atoms or a hydrogen atom;
n is an integer of 1 to 4;
when n is an integer of 2 to 4, n $R^1$s may be the same or different and n $R^2$s may be the same or different); and
compounds represented by formula (2):

(wherein Y represents an alkaline earth metal, and $R^1$, $R^2$, and n are as defined above), and the methylene disulfonate compound being represented by formula (3):

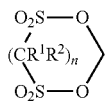 (3)

(wherein $R^1$, $R^2$, and n are as defined above).

Item 2

The method for producing a methylene disulfonate compound according to Item 1, wherein the formaldehyde compound is at least one member selected from the group consisting of paraformaldehyde, anhydrous formaldehyde, trioxane, and methylal.

Item 3

The method for producing a methylene disulfonate compound according to Item 1 or 2, wherein the sulfonic acid compound is a compound of formula (1) wherein two Xs are both a hydrogen atom.

Item 4

The method for producing a methylene disulfonate compound according to any one of Items 1 to 3, wherein the reaction of the sulfonic acid compound with the formaldehyde compound is performed in the presence of sulfur trioxide and a dehydrating agent.

Item 5

The method for producing a methylene disulfonate compound according to Item 4, wherein the dehydrating agent is phosphorus pentoxide.

Advantageous Effects of Invention

A production method that enables easy and inexpensive production of a methylene disulfonate compound is provided. This production method is industrially advantageous because the viscosity of the reaction mixture during the production process is relatively low and the reaction mixture exhibits good handleability even in industrial-scale production.

DESCRIPTION OF EMBODIMENTS

Embodiments included in the present disclosure are described in more detail below. The present disclosure preferably includes a method for producing a methylene disulfonate compound etc., but is not limited thereto. The present disclosure includes everything that is disclosed in the present specification and recognizable to those skilled in the art.

The method for producing a methylene disulfonate compound included in the present disclosure comprises reacting a specific sulfonic acid compound with a formaldehyde compound in the presence of sulfur trioxide.

The specific sulfonic acid compound is at least one compound selected from the group consisting of compounds represented by formula (1) and compounds represented by formula (2).

 (1)

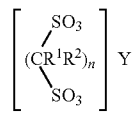 (2)

In formulas (1) and (2), $R^1$ and $R^2$ independently (i.e., may be the same or different) represent a $C_{1-4}$ ($C_1$, $C_2$, $C_3$, or $C_4$) alkyl group optionally substituted with one or more halogen atoms or a hydrogen atom, and n is an integer of 1 to 4 (1, 2, 3, or 4). Xs are the same or different (preferably the same) and represent a hydrogen atom or an alkali metal, and Y represents an alkaline earth metal.

Examples of halogen atoms in the $C_{1-4}$ alkyl group optionally substituted with one or more halogen atoms include a fluorine atom, a chlorine atom, a bromine atom, and the like. Specific examples of the $C_{1-4}$ alkyl group optionally substituted with one or more halogen atoms include methyl, ethyl, n-propyl, iso-propyl, n-butyl, iso-butyl, sec-butyl, tert-butyl, fluoromethyl, trifluoromethyl, chloromethyl, chloroethyl, chloropropyl, bromomethyl, and the like.

$R^1$ and $R^2$ preferably represent a hydrogen atom, methyl, ethyl, and n-propyl, and more preferably a hydrogen atom.

In each of formula (1) and formula (2), when n is an integer of 2 to 4 (2, 3, or 4), n $R^1$s may be the same or different, and n $R^2$s may be the same or different; and n is preferably 1.

Examples of alkali metals represented by X include lithium, sodium, potassium, and the like.

Examples of alkaline earth metals represented by Y include magnesium, calcium, barium, and the like.

The specific sulfonic acid compound is preferably a compound of formula (1) wherein two Xs are the same or different and represent a hydrogen atom, sodium, or potassium, and more preferably a compound of formula (1) wherein two Xs are both a hydrogen atom.

Specific examples of sulfonic acid compounds represented by formula (1) include the following compounds.

Methanedisulfonic acid (X=H, $R^2$=$R^2$=H, n=1), 1,1-ethanedisulfonic acid (X=H, $R^1$=$CH_3$, $R^2$=H, n=1), 1,2-ethanedisulfonic acid (X=H, $R^1$=$R^2$=H, n=2), 1,1-propanedisulfonic acid (X=H, $R^1$=$CH_2CH_3$, $R^2$=H, n=1), 1,2-propanedisulfonic acid (X=H, $R^1$=$CH_3$ and H, $R^2$=H, n=2), 1,3-propanedisulfonic acid (X=H, $R^1$=$R^2$=H, n=3), 2,2-propanedisulfonic acid (X=H, $R^1$=$R^2$=$CH_3$, n=1), 1,4-butanedisulfonic acid (X=H, $R^1$=$R^2$=H, n=4), sodium methanedisulfonate (X=Na, $R^1$=$R^2$=H, n=1), sodium 1,1-ethanedisulfonate (X=Na, $R^1$=$CH_3$, $R^2$=H, n=1), sodium 1,2-ethanedisulfonate (X=Na, $R^1$=$R^2$=H, n=2), sodium 1,1-propanedisulfonate (X=Na, $R^1$=$CH_2CH_3$, $R^2$=H, n=1, sodium 1,2-propanedisulfonate (X=Na, $R^1$=$CH_3$ and H, $R^2$=H, n=2), sodium 1,3-propanedisulfonate (X=Na, $R^1$=$R^2$=H, n=3), sodium 2,2-propanedisulfonate (X=Na, $R^1$=$R^2$=$CH_3$, n=1), sodium 1,4-butanedisulfonate (X=Na, $R^1$=$R^2$=H, n=4), potassium methanedisulfonate (X=K, $R^1$=$R^2$=H, n=1), potassium 1,1-ethanedisulfonate (X=K, $R^1$=$CH_3$, $R^2$=H, n=1), potassium 1,2-ethanedisulfonate (X=K, $R^1$=$R^2$=H, n=2), potassium 1,1-potassium propane disulfonate (X=K, $R^1$=$CH_2CH_3$, $R^2$=H, n=1), potassium 1,2-propanedisulfonate (X=K, $R^1$=$CH_3$ and H, $R^2$=H, n=2), potassium 1,3-propanedisulfonate (X=K, $R^1$=$R^2$=H, n=3), potassium 2,2-propanedisulfonate (X=K, $R^1$=$R^2$=$CH_3$, n=1), and potassium 1,4-butanedisulfonate (X=K, $R^1$=$R^2$=H, n=4).

Specific examples of sulfonic acid compounds represented by formula (2) include the following compounds.

Calcium methanedisulfonate (Y=Ca, $R^1$=$R^2$=H, n=1), calcium 1,2-ethanedisulfonate (Y=Ca, $R^1$=$R^2$=H, n=2), magnesium methanedisulfonate (Y=Mg, $R^1$=$R^2$=H, n=1), barium methanedisulfonate (Y=Ba, $R^1$=$R^2$=H, n=1), barium 1,2-ethanedisulfonate (Y=Ba, $R^1$=$R^2$=H, n=2), barium 1,2-propanedisulfonate (Y=Ba, $R^1$=$CH_3$ and H, $R^2$=H, n=2), barium 1,3-propanedisulfonate (Y=Ba, $R^1$=$R^2$=H, n=3), and barium 1,4-butanedisulfonate (Y=Ba, $R^1$=$R^2$=H, n=4).

The sulfonic acid compound may be a commercially available product, or may be prepared by a known method or a method readily conceivable from known methods. For example, the sulfonic acid compound can be prepared by a method comprising reacting the corresponding disulfonyl halide with water with reference to JP2005-336155A. Alternatively, the sulfonic acid compound can also be prepared by reacting dichloromethane with an alkali salt of sulfurous acid in an aqueous solvent at 150 to 160° C. with reference to Recueil des Travaux Chimiques des Pays-Bas, 48, 949-952 (1929).

Such sulfonic acid compounds can be used singly or in a combination of two or more.

Examples of the formaldehyde compound include paraformaldehyde, formaldehyde anhydride, trioxane, acetalated formaldehydes (e.g., methylal), and the like. Anhydrous formaldehyde can be obtained, for example, by subjecting paraformaldehyde to heat treatment. Trioxane can be obtained, for example, by subjecting paraformaldehyde to acid treatment. Among these, the formaldehyde compound is preferably paraformaldehyde, formaldehyde anhydride, or trioxane, and more preferably paraformaldehyde. The formaldehyde compounds can be used singly or in a combination of two or more.

The amount of the formaldehyde compound to be used can be, for example, 0.6 to 10 moles, preferably 0.7 to 7.0 moles, and more preferably 0.8 to 5.0 moles, per 1.0 mole of the sulfonic acid compound.

When the amount of the formaldehyde compound used is 0.6 moles or more, the reaction fully proceeds and an increased yield can be obtained. Further, when the amount used is 10 moles or less, it is economical.

The amount of the sulfur trioxide used can be, for example, 0.1 to 10 moles, preferably 0.2 to 8.0 moles, and more preferably 0.3 to 6.0 moles, per 1.0 mole of the sulfonic acid compound.

When the amount of the sulfur trioxide used is 0.1 moles or more, the reaction fully proceeds, and an increased yield can be obtained. When the amount of the sulfur trioxide used is 10 moles or less, it is economical.

In the reaction of the specific sulfonic acid compound and formaldehyde compound in the presence of sulfur trioxide, a dehydrating agent may be additionally used for the purpose of promoting the reaction. Examples of dehydrating agents include phosphorus pentoxide, phosphorus pentachloride, phosphorus oxychloride, thionyl chloride, acetyl chloride, acetic anhydride, aluminum chloride, and the like. Among these, phosphorus pentoxide is preferably used from the viewpoint of reactivity. The dehydrating agents can be used singly or in a combination of two or more.

The amount of the dehydrating agent to be used can be 0 to 10 moles, preferably 0 to 5.0 moles, and more preferably 0 to 3.0 moles, per 1.0 mole of the sulfonic acid compound.

The lower limit of the range of the amount of the dehydrating agent is not particularly limited, and can be, for example, about 0.1, 0.5, or 1 mole.

In the above reaction, a solvent may be used as necessary. The amount of the solvent used can be, for example, 0 to 1500 parts by mass, and preferably 0 to 1000 parts by mass, per 100 parts by mass of the sulfonic acid compound. The lower limit of the range of the amount of the solvent is not limited, but can be, for example, about 1, 5, or 10 parts by mass.

Examples of solvents include hydrocarbon solvents, ether solvents, ketone solvents, ester solvents, amide solvents, nitrile solvents, sulfoxide solvents, sulfone solvents, sulfuric acid, and the like. Examples of hydrocarbon solvents include toluene, xylene, monochlorobenzene, dichlorobenzene, trichlorobenzene, hexane, heptane, decane, and the like. Examples of ether solvents include diethyl ether, ethylene glycol dimethyl ether, diisopropyl ether, diphenyl ether, tetrahydrofuran, dioxane, methyl-tert-butyl ether, cyclopentyl methyl ether, and the like. Examples of ketone solvents include acetone, methyl ethyl ketone, methyl isobutyl ketone, and the like. Examples of ester solvents include ethyl acetate, butyl acetate, and the like. Examples of amide solvents include dimethylformamide, dimethylacetamide, N-methylpyrrolidone, and the like. Examples of nitrile solvents include acetonitrile and the like. Examples of sulfoxide solvents include dimethylsulfoxide and the like. Examples of sulfonic solvents include ethylmethylsulfone, ethylisopropylsulfone, sulfolane, 3-methylsulfolane, and the like.

Among them, preferable solvents are ether solvents, ketone solvents, ester solvents, amide solvents, nitrile solvents, sulfoxide solvents, sulfone solvents, and sulfuric acid; more preferably sulfoxide solvents, sulfone solvents, and sulfuric acid; and even more preferably sulfoxide solvents and sulfone solvents.

In the reaction of the specific sulfonic acid compound and formaldehyde compound in the presence of sulfur trioxide, the reaction method is not particularly limited. Examples of reaction methods include a method comprising placing a sulfonic acid compound and sulfur trioxide optionally together with a solvent and/or a dehydrating agent in a reaction vessel and adding paraformaldehyde while the mixture is stirred well; a method comprising placing a sulfonic acid compound and a formaldehyde compound optionally together with a solvent and/or a dehydrating agent in a reaction vessel and adding sulfur trioxide while the mixture is stirred well; and a method comprising placing a paraformaldehyde compound and sulfur trioxide optionally together with a solvent and/or a dehydrating agent in a reaction vessel, and adding a sulfonic acid compound while the mixture is stirred well; and the like.

The above reaction temperature can be, for example, about 0 to 200° C., and is preferably about 10 to 150° C. The reaction time may vary depending on the reaction temperature; however, it is, for example, about 0.1 to 20 hours.

The above method can produce a methylene disulfonate compound represented by formula (3):

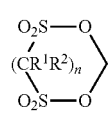

(3)

(wherein $R^1$, $R^2$ and n are as defined above).

Specific examples of methylene disulfonate compounds represented by formula (3) include methylene methanedisulfonate ($R^1=R^2=H$, n=1), methylene 1,1-ethanedisulfonate ($R^1=CH_3$, $R^2=H$, n=1), methylene 1,2-ethanedisulfonate ($R^1=R^2=H$, n=2), methylene 1,1-propanedisulfonate ($R^1=CH_2CH_3$, $R^2=H$, n=1), methylene 1,2-propanedisulfonate ($R^1=CH_3$ and H, $R^2=H$, n=2), methylene 1,3-propanedisulfonate ($R^1=R^2=H$, n=3), methylene 2,2-propanedisulfonate ($R^1=CH_3$, $R^2=CH_3$, n=1), methylene 1,4-butanedisulfonate ($R^1=R^2=H$, n=4), and the like.

The methylene disulfonate compound obtained by the above method can be isolated, for example, by conventional known purification and isolation operations. The method for purification and isolation is not particularly limited. Examples of usable methods include a method comprising subjecting the reaction mixture to extraction using a solvent or the like, then washing with water or the like, and performing crystallization; a method comprising adding water or the like to the reaction mixture and decomposing sulfur trioxide and then, as described above, subjecting the reaction mixture to extraction with a solvent, washing with water or the like, and performing crystallization; and a method comprising adding a poor solvent, such as water, to the reaction mixture, precipitating a crude product, separating the precipitate by filtration, and recrystallizing the filtrate for purification.

The term "comprising" as used herein includes "consisting essentially of" and "consisting of." Further, the present disclosure includes any and all combinations of the components described in the present specification.

Various characteristics (properties, structures, functions, etc.) described in the above embodiments of the present disclosure may be combined in any manner to specify the subject matter included in the present disclosure. That is, this disclosure includes all of the subject matter comprising any combination of the combinable properties described herein.

EXAMPLES

The embodiments of the present disclosure are more specifically explained below with reference to Examples; however, the embodiments are not limited to the Examples shown below.

Example 1

17.6 g (0.10 moles) of methanedisulfonic acid, 10.0 g of sulfolane, and 16.0 g (0.20 moles) of sulfur trioxide were placed in a four-necked flask equipped with a stirrer, a cooling tube, a thermometer, and a dropping funnel. After 3.3 g of 91% paraformaldehyde (0.10 moles in terms of formaldehyde) was added with stirring at room temperature, the mixture was stirred at 55° C. for 3 hours. The yield of methylene methanedisulfonate was 73 mol % relative to methanedisulfonic acid. The yield of methylene methanedisulfonate was determined from the peak area value obtained by sampling the reaction mixture and performing HPLC analysis (the same applies to the following examples).

Subsequently, the reaction mixture was cooled to 25° C. The viscosity of the reaction mixture was low even at 25° C., and the reaction mixture had excellent flowability.

Subsequently, methylene chloride and water were added to the reaction mixture, and the resulting mixture was subjected to liquid-liquid separation. The obtained organic layer was washed with water and concentrated. The precipitated crystals were separated by filtration and dried at 40° C. at 10 mmHg for 6 hours to obtain 12.2 g of methylene methanedisulfonate. The yield of methylene methanedisulfonate was 65 mol % relative to methanedisulfonic acid.

$^1$H-NMR analysis confirmed that the obtained crystals were methylene methanedisulfonate.

$^1$H-NMR (400 MHz, $CD_3CN$) δ(ppm): 5.33 (s, 2H), 6.00 (s, 2H).

Example 2

17.6 g (0.10 moles) of methanedisulfonic acid, 10.0 g of sulfolane, and 16.0 g (0.20 moles) of sulfur trioxide were placed in a four-necked flask equipped with a stirrer, a cooling tube, a thermometer, and a dropping funnel. After 3.3 g of 91% paraformaldehyde (0.10 moles in terms of formaldehyde) was added with stirring at room temperature, the mixture was stirred at 40° C. for 3 hours. The yield of methylene methanedisulfonate was 80 mol % relative to methanedisulfonic acid.

Subsequently, the reaction mixture was cooled to 25° C. The viscosity of the reaction mixture was low even at 25° C., and the reaction mixture had excellent flowabillty.

Example 3

17.6 g (0.10 moles) of methanedisulfonic acid, 10.0 g of sulfolane, and 16.0 g (0.20 moles) of sulfur trioxide were placed in a four-necked flask equipped with a stirrer, a cooling tube, a thermometer, and a dropping funnel. After 3.3 g of 91% paraformaldehyde (0.10 moles in terms of formaldehyde) was added with stirring at room temperature, the mixture was stirred at 30° C. for 3 hours. The yield of methylene methanedisulfonate was 82 mol % relative to methanedisulfonic acid.

Subsequently, the reaction mixture was cooled to 25° C. The viscosity of the reaction mixture was low even at 25° C., and the reaction mixture had excellent flowability.

Example 4

17.6 g (0.10 moles) of methanedisulfonic acid, 10.0 g of sulfolane, and 24.0 g (0.30 moles) of sulfur trioxide were placed in a four-necked flask equipped with a stirrer, a cooling tube, a thermometer, and a dropping funnel. After 3.3 g of 91% paraformaldehyde (0.10 moles in terms of formaldehyde) was added with stirring at room temperature, the resulting mixture was stirred at 55° C. for 1 hour. The yield of methylene methanedisulfonate was 80 mol % relative to methanedisulfonic acid.

Subsequently, the reaction mixture was cooled to 25° C. The viscosity of the reaction mixture was low even at 25° C., and the reaction mixture had excellent flowability.

Example 5

17.6 g (0.10 moles) of methanedisulfonic acid, 10.0 g of sulfolane, and 27.2 g (0.34 moles) of sulfur trioxide were placed in a four-necked flask equipped with a stirrer, a cooling tube, a thermometer, and a dropping funnel. After 5.6 g (0.17 moles in terms of formaldehyde) of 91% paraformaldehyde was added with stirring at room temperature, the resulting mixture was stirred at 55° C. for 3 hours. The yield of methylene methanedisulfonate was 90 mol % relative to methanedisulfonic acid.

Subsequently, the reaction mixture was cooled to 25° C. The viscosity of the reaction mixture was low even at 25° C., and the reaction mixture had excellent flowability.

Example 6

17.6 g (0.10 moles) of methanedisulfonic acid, 60.0 g of sulfolane, and 38.4 g (0.48 moles) of sulfur trioxide were placed in a four-necked flask equipped with a stirrer, a cooling tube, a thermometer, and a dropping funnel. After 13.2 g of 91% paraformaldehyde (0.40 moles in terms of formaldehyde) was added with stirring at room temperature, the resulting mixture was stirred at 100° C. for 2 hours. The yield of methylene methanedisulfonate was 86 mol % relative to methanedisulfonic acid.

Subsequently, the reaction mixture was cooled to 25° C. The viscosity of the reaction mixture was low even at 25° C., and the reaction mixture had excellent flowability.

Example 7

17.6 g (0.10 moles) of methanedisulfonic acid, 40.0 g of sulfolane, 19.2 g (0.24 moles) of sulfur trioxide, and 7.1 g of phosphorus pentoxide (0.05 moles in terms of $P_2O_5$) were placed in a four-necked flask equipped with a stirrer, a cooling tube, a thermometer, and a dropping funnel. After 6.6 g of 91% paraformaldehyde (0.20 moles in terms of formaldehyde) was added with stirring at room temperature, the resulting mixture was stirred at 100° C. for 2 hours. The yield of methylene methanedisulfonate was 74 mol % relative to methanedisulfonic acid.

Subsequently, the reaction mixture was cooled to 25° C. The viscosity of the reaction mixture was low even at 25° C., and the reaction mixture had excellent flowability.

Example 8

17.6 g (0.10 moles) of methanedisulfonic acid and 24.0 g (0.30 moles) of sulfur trioxide were placed in a four-necked flask equipped with a stirrer, a cooling tube, a thermometer, and a dropping funnel. After 3.3 g of 91% paraformaldehyde (0.10 moles in terms of formaldehyde) was added with stirring at room temperature, the resulting mixture was stirred at 5° C. for 2 hours. The yield of methylene methanedisulfonate was 47 mol % relative to methanedisulfonic acid.

Subsequently, the reaction mixture was cooled to 25° C. The viscosity of the reaction mixture was low even under 25° C., and the reaction mixture had excellent flowability.

Example 9

17.6 g (0.10 moles) of methanedisulfonic acid, 10.0 g (0.10 moles) of dimethyl sulfoxide, and 24.0 g (0.30 moles) of sulfur trioxide were placed in a four-necked flask equipped with a stirrer, a cooling tube, a thermometer, and a dropping funnel. After 3.3 g of 91% paraformaldehyde (0.10 moles in terms of formaldehyde) was added with stirring at room temperature, the resulting mixture was stirred at 55° C. for 1 hour. The yield of methylene methanedisulfonate was 64 mol % relative to methanedisulfonic acid.

Subsequently, the reaction mixture was cooled to 25° C. The viscosity of the reaction mixture was low even at 25° C., and the reaction mixture had excellent flowability.

Example 10

17.6 g (0.10 moles) of methanedisulfonic acid, 80.0 g of sulfolane, and 64.1 g of 60% fuming sulfuric acid (sulfuric acid containing 60 mass % of sulfur trioxide) (36.4 g in terms of sulfur trioxide, corresponding to 0.48 moles, and 25.6 g in terms of sulfuric acid) were placed in a four-necked flask equipped with a stirrer, a cooling tube, a thermometer, and a dropping funnel. After 3.3 g of 91% paraformaldehyde (0.10 moles in terms of formaldehyde) was added with stirring at room temperature, the resulting mixture was stirred at 55° C. for 1 hour. The yield of methylene methanedisulfonate was 69 mol % relative to methanedisulfonic acid.

Subsequently, the reaction mixture was cooled to 25° C. The viscosity of the reaction mixture was low even at 25° C., and the reaction mixture had excellent flowability.

Example 11

17.6 g (0.10 moles) of methanedisulfonic acid and 40.0 g of 60% fuming sulfuric acid (sulfuric acid containing 60 mass % sulfur trioxide) (24.0 g in terms of sulfur trioxide, corresponding to 0.30 moles, 16.0 g in terms of sulfuric acid) were placed in a four-necked flask equipped with a stirrer, a cooling tube, a thermometer, and a dropping funnel. After 3.3 g of 91% paraformaldehyde (0.10 moles in terms of formaldehyde) was added with stirring at room temperature, the resulting mixture was stirred at 55° C. for 1 hour. The yield of methylene methanedisulfonate was 47 mol % relative to methanedisulfonic acid.

Subsequently, the reaction mixture was cooled to 25° C. The viscosity of the reaction mixture was low even under 25° C., and the reaction mixture had excellent flowability.

The above results show that according to the above production method, the reaction can favorably proceed without incurring precipitation of by-products or an increase in the viscosity of the reaction mixture with the progress of the reaction. That is, the production method enables easy and inexpensive production of a methylene disulfonate compound without incurring handling problems such as deterioration of stirring during the reaction and an increase in transfer load, thus being suitable for industrial-scale production.

The invention claimed is:

1. A method for producing a methylene disulfonate compound, the method comprising reacting at least one sulfonic acid compound with a formaldehyde compound in the presence of sulfur trioxide,
   the amount of sulfur trioxide being 2.0 to 10 moles per 1.0 mole of the sulfonic acid compound,
   the sulfonic acid compound being selected from the group consisting of:
   compounds represented by formula (1):

wherein two Xs are the same or different and represent a hydrogen atom or an alkali metal;
$R^1$ and $R^2$ are the same or different and represent a $C_{1-4}$ alkyl group optionally substituted with one or more halogen atoms or a hydrogen atom;
n is an integer of 1 to 4;
when n is an integer of 2 to 4, n $R^1$s may be the same or different and n $R^2$s may be the same or different; and compounds represented by formula (2):

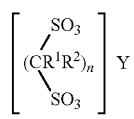 (2)

wherein Y represents an alkaline earth metal, and $R^1$, $R^2$, and n are as defined above, and the methylene disulfonate compound being represented by formula (3):

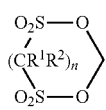 (3)

wherein $R^1$, $R^2$, and n are as defined above.

2. The method for producing a methylene disulfonate compound according to claim 1, wherein the formaldehyde compound is at least one member selected from the group consisting of paraformaldehyde, anhydrous formaldehyde, trioxane, and methylal.

3. The method for producing a methylene disulfonate compound according to claim 1, wherein the sulfonic acid compound is a compound of formula (1) wherein two Xs are both a hydrogen atom.

4. The method for producing a methylene disulfonate compound according to claim 1, wherein the reaction of the sulfonic acid compound with the formaldehyde compound is performed in the presence of sulfur trioxide and a dehydrating agent.

5. The method for producing a methylene disulfonate compound according to claim 4, wherein the dehydrating agent is phosphorus pentoxide.

* * * * *